US00PP27739P3

(12) United States Plant Patent
Olesen

(10) Patent No.: US PP27,739 P3
(45) Date of Patent: Mar. 7, 2017

(54) COMPACT FLORIBUNDA ROSE PLANT NAMED 'POULPAL059'

(50) Latin Name: ***Rosa* hybrid**
Varietal Denomination: Poulpal059

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 183 days.

(21) Appl. No.: 14/121,289

(22) Filed: Aug. 15, 2014

(65) Prior Publication Data

US 2016/0050818 P1 Feb. 18, 2016

(51) Int. Cl.
*A01H 5/02* (2006.01)

(52) U.S. Cl.
USPC ..... Plt./150

(58) Field of Classification Search
USPC ..... Plt./150
See application file for complete search history.

*Primary Examiner* — Keith Robinson

(57) ABSTRACT

A new garden rose plant of the Compact Floribunda class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal059'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulpal059', originated as a single seedling from the stated cross.

The new variety may be distinguished from its male pollen parent and female seed parent primarily by the following characteristics. The female seed parent has flowers which are a blend of red, yellow, and orange, while the new plant has red flowers. The male pollen parent also has red flowers, however the new variety has more flower buds per flowering branch than the male pollen parent variety.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal059' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulpal059' was selected in the spring of 2005 by the inventor as a single plant from the progeny of the aforementioned hybridization.

Asexual reproduction of 'Poulpal059' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulpal059' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal059'. Specifically illustrated in FIG. 1 are flowers at various stages of development, flower in parts, and a cluster of open flowers, FIG. 2 are leaves, and stems. Plants shown are 2 years of age.

DETAILED DESCRIPTION OF THE VARIETY

Figure 1:
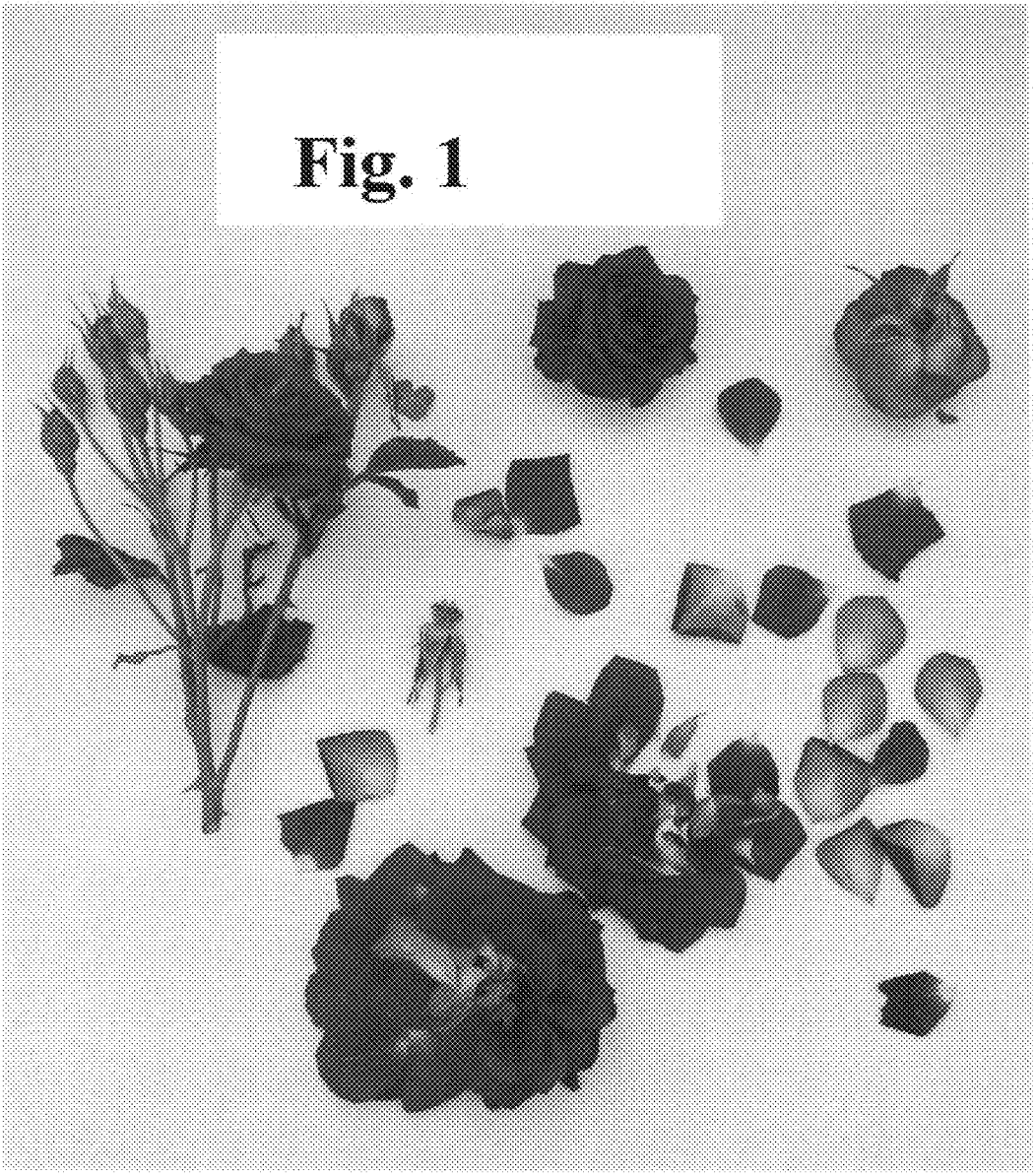
Figure 2:
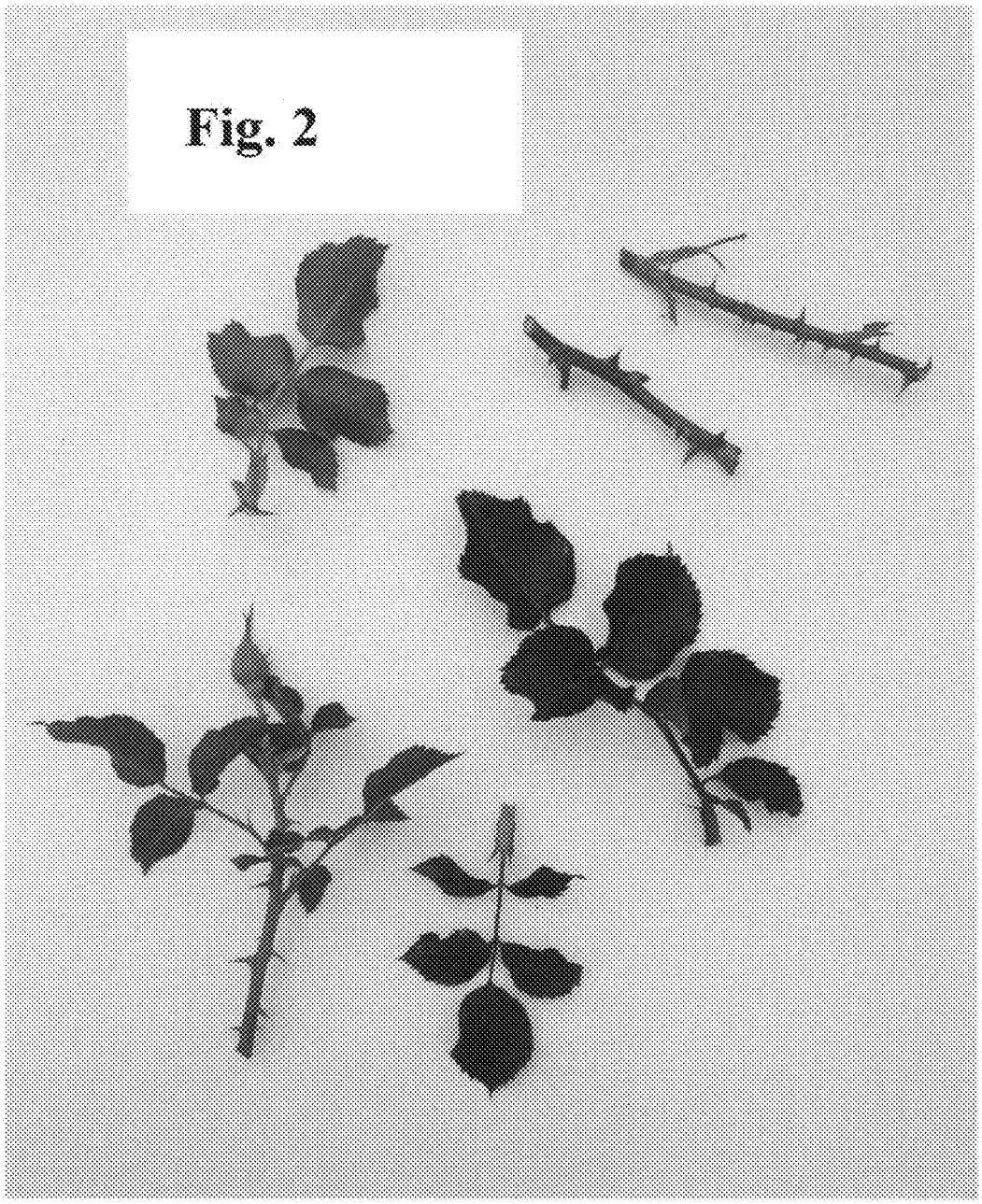

The following is a description of 'Poulpal059', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulchris', U.S. Plant Pat. No. 11,151 are compared to 'Poulpal059' in Chart 1.

CHART 1

| | 'Poulpal059' | 'Poulchris' |
|---|---|---|
| Petal Count | 35 to 40 | 55 to 65 |
| Flower Diameter | 55 mm | 60 mm |

CHART 1-continued

| | 'Poulpal059' | 'Poulchris' |
|---|---|---|
| Flower Color, upper petal surface after opening | Red Group 46A | Red Group 53A |

FLOWER AND FLOWER BUD

Blooming habit: Continuous.

Flower bud:

*Size.*—Upon opening, 20 mm in length from base of receptacle to end of bud. Bud diameter is 10 mm.

*Bud form.*—Ovoid.

*Bud color.*—As sepals divide Red-Purple Group 63A and Yellow-Green Group149C.

*Sepal inner surface.*—Color: Yellow-Green Group 144A with intonations of Greyed-Red Group 179A. Surface: Smooth and Pubescent.

*Sepal outer surface.*—Color: Yellow-Green Group 144A with intonations of Greyed-Red Group 178A. Texture: Smooth.

*Sepal shape.*—Apex: Cirrhose. Base: Flat at union with receptacle.

*Sepal margin.*—Margins have strong weak foliaceous appendages on three of the five sepals.

*Sepal size.*—28 mm long by 10 mm wide.

*Receptacle.*—Texture: Smooth. Size: 6 mm in height by 6 mm wide. Color: Yellow-Green Group 144B. Shape: Campanulate.

*Pedicel.*—Surface: Smooth. Length: 35 mm. Diameter: 2 mm on average. Color: Yellow-Green Group 144A. Strength: Strong.

*Peduncle.*—Length: 80 to 90 mm. Diameter: 3 to 4 mm. Texture: Smooth. Coloration: Yellow-Green Group 144A.

Flower bud development: Flower buds are borne in clusters of 5 to 12 flower buds per stem, resembling a corymb.

Flower bloom:

*Fragrance.*—Moderate to strong old rose scent.

*Duration.*—The blooms have a duration on the plant of approximately 7 to 10 days. Petals fall cleanly away from plant after flowers have fully matured.

*Size.*—Flower diameter is 55 mm when open. Flower depth is 25 mm.

*Flower shape.*—Double. General shape is a rosette with many slightly overlapping petals of different sizes.

*Shape of flower, side view.*—The upper portion is a flattened convex, and the lower portion is a flattened convex.

Petalage: Under normal conditions, flowers have 35 to 40 petals total, 3 of which are petaloids.

General tonality of flower: Open flowers are Red Group 46A.

Petal color:

*Upon opening, inner and outer petals.*—Upper surface: Red Group 46A with a petal spot of Yellow Group 4A at the base about 3 to 5 mm in length. Lower surface: Red-Purple Group 61B splashed with Red-Purple Group 62D.

*After opening, outer and inner petals.*—Upper surface: Red Group 46A with a petal spot of Yellow Group 4A at the base about 3 to 5 mm in length. Lower surface: Red-Purple Group 61B splashed with Red-Purple Group 62D.

Petals:

*Petal reflex.*—Strong bi-lateral reflex.

*Margin.*—Entire and uniform with a slight point at the center of the apex. Weak undulations of margin observed.

*Shape.*—Generally rounded. Apex shape: Rounded. Base shape: Acute.

*Size.*—25 mm (l)×25 mm (w).

*Texture.*—Smooth on both upper and lower surfaces.

*Thickness.*—Average.

Petaloids:

*Size.*—15 mm (l) by 10 mm (w).

*Quantity.*—About 3.

*Shape.*—Kidney bean.

*Color.*—Upper, Red Group 46A with a spot of Yellow Group 4A at the base. Lower, Red-Purple Group 61B splashed with Red-Purple Group 62D.

Reproductive organs:

*Pollen.*—None observed.

*Anthers.*—Size: 2 mm in length. Color: Yellow Group 11A. Quantity: 15 on average.

*Filaments.*—Color: Yellow Group 11C. Length: 2 to 3 mm.

*Pistils.*—Length: 4 mm. Quantity: 20 on average.

*Stigmas.*—Color: Greyed-Yellow Group 160D.

*Styles.*—Color: Greyed-Yellow Group 160D.

*Location of stigmas.*—Superior in location relative to the length of the filaments and the height of the anthers.

*Hips.*—None Observed.

PLANT

Plant growth: Upright, bushy. Plants are 40 to 45 cm in height, and 40 to 45 cm wide.

Stems:

*Color.*—Juvenile growth: Yellow-Green Group 146C with light intonations of Greyed-Red Group 178A. Mature growth: Yellow-Green Group 144A.

*Length.*—On average, canes are 20 cm from the base of the plant to the flowering portion.

*Diameter.*—About 9 mm.

*Internodes.*—On mature canes, there is an average distance of 50 mm between nodes.

*Surface texture.*—Young wood: Smooth. Older wood: Smooth.

Long prickles:

*Incidence.*—8 prickles per 10 cm of stem.

*Size.*—Average length of prickles on mature stems is 8 mm.

*Shape.*—Upper portion is linear. Lower portion is concave.

*Color.*—Juvenile prickles: Greyed-Red Group 182B. Mature prickles: Greyed-Yellow Group 162B.

Plant foliage:

*Compound leaf.*—110 mm (l)×75 (w).

*Quantity.*—2 to 3 leaves per 10 cm of stem on average.

*Color of juvenile foliage.*—Upper side: Yellow-Green Group 147A mixed with Greyed-Purple Group 187A. Lower side: Greyed-Purple Group 183B.

*Color of mature foliage*.—Upper side: Yellow-Green Group 147A. Lower side: Yellow-Green Group 147C.

Plant leaves and leaflets:

*Stipules*.—Size: 15 mm in length. Quantity: 2 per compound leaf. Shape: Linear, slightly broad based with outward extending apices. Margins: Finely serrated. Color: Yellow-Green Group 148A.

*Petiole*.—Length: 20 mm. Diameter: 1 mm.

*Upper surface*.—Color: Greyed-Purple Group 184B.

*Lower surface*.—Color: Greyed-Purple Group 184B with Yellow-Green Group 146C.

*Rachis*.—Length: 40 mm. Upper surface: Color: Yellow-Green Group 144A.

*Lower surface*.—Color: Yellow-Green Group 146C.

*Leaflet*.—Quantity: Normally 5 leaflets. Margins: Doubly serrated. Size: Average size of the terminal leaflet on normal leaves is 40 mm in length by 35 mm wide. Shape: Generally ovate. Base: Rounded. Apex: Mucronate. Texture: Smooth on both upper and lower surfaces. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulpal059', substantially as illustrated and described herein, due to its abundant red flowers, disease resistance, and extended period of bloom.

* * * * *